US012385394B1

(12) United States Patent
Wei et al.

(10) Patent No.: US 12,385,394 B1
(45) Date of Patent: Aug. 12, 2025

(54) HYDROCARBON EXPLORATION AND PRODUCTION USING POROSITY VARIATION PREDICTION BASED ON CARBONATE TEXTURE

(71) Applicant: Saudi Arabian Oil Company, Dhahran (SA)

(72) Inventors: Wei Wei, Beijing (CN); Peng Lu, Dhahran (SA); Yufeng Cui, Beijing (CN); Rainer Zuhlke, Dhahran (SA); David Tang, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 18/784,085

(22) Filed: Jul. 25, 2024

(51) Int. Cl.
E21B 49/00 (2006.01)
G01N 15/08 (2006.01)
G01N 33/24 (2006.01)

(52) U.S. Cl.
CPC ......... *E21B 49/005* (2013.01); *G01N 15/088* (2013.01); *G01N 33/24* (2013.01)

(58) Field of Classification Search
CPC .... E21B 49/005; G01N 15/088; G01N 33/24; G01N 33/241
See application file for complete search history.

(56) References Cited

U.S. PATENT DOCUMENTS

| 4,542,648 A | 9/1985 | Vinegar et al. |
| 6,088,656 A | 7/2000 | Ramakrishnan et al. |
| 6,229,308 B1 | 5/2001 | Freedman |
| 6,977,499 B2 | 12/2005 | Kiesl et al. |
| 6,987,385 B2 | 1/2006 | Akkurt et al. |
| 7,363,158 B2 | 4/2008 | Stelting et al. |
| 7,970,545 B2 | 6/2011 | Sanstrom |
| 8,385,604 B2 | 2/2013 | Orpen |
| 8,605,951 B2 | 12/2013 | Baggs et al. |

(Continued)

FOREIGN PATENT DOCUMENTS

CN 106841001 6/2017

OTHER PUBLICATIONS

Athy, "Density, Porosity, and Compaction of Sedimentary Rocks," Bulletin of the American Association of Petroleum Geologists, Jan. 1930, 14(1), 24 pages.

(Continued)

*Primary Examiner* — Shane Bomar
(74) *Attorney, Agent, or Firm* — Fish & Richardson P.C.

(57) ABSTRACT

A method for hydrocarbon production from a carbonate formation includes receiving a carbonate texture description of a drill cutting. A pre-defined grain fraction is assigned to the drill cutting based on the texture description. The pre-defined grain fraction is one of a set of pre-defined grain fractions and each pre-defined grain fraction of the set of pre-defined grain fractions corresponds to a respective one the set of carbonate texture descriptions. Based on the pre-defined grain fraction assigned to the drill cutting and a depth of the wellbore from which the drill cutting is taken, an estimated porosity of the drill cutting is determined using an algebraic equation, coefficients for which are determined by regression analysis using reference rock samples that have been assigned pre-defined grain fractions from the same set of pre-defined grain fractions.

16 Claims, 7 Drawing Sheets

(56) References Cited

U.S. PATENT DOCUMENTS

| | | | |
|---|---|---|---|
| 9,081,117 B2 | 7/2015 | Wu et al. | |
| 9,483,871 B2 | 11/2016 | Sung et al. | |
| 11,047,228 B2 | 6/2021 | Zhang et al. | |
| 11,435,494 B1 | 9/2022 | Wang et al. | |
| 11,592,593 B2 | 2/2023 | Alkhaldi | |
| 2007/0239359 A1 | 10/2007 | Stelting et al. | |
| 2010/0135536 A1 | 6/2010 | Dvorkin et al. | |
| 2010/0198638 A1 | 8/2010 | Deffenbaugh et al. | |
| 2010/0305927 A1 | 12/2010 | Suarez-Rivera et al. | |
| 2011/0270594 A1 | 11/2011 | Rudnicki | |
| 2012/0221306 A1 | 8/2012 | Hurley et al. | |
| 2013/0080133 A1 | 3/2013 | Sung et al. | |
| 2013/0140031 A1 | 6/2013 | Cohen et al. | |
| 2013/0259190 A1 | 10/2013 | Walls et al. | |
| 2013/0297272 A1 | 11/2013 | Sung et al. | |
| 2014/0067351 A1 | 3/2014 | Gray et al. | |
| 2017/0018073 A1* | 1/2017 | Sungkorn | G06F 18/24 |
| 2017/0314385 A1* | 11/2017 | Hori | E21B 47/12 |
| 2018/0188403 A1 | 7/2018 | Halsey et al. | |
| 2020/0123898 A1* | 4/2020 | Zhang | G06Q 10/04 |
| 2022/0380657 A1* | 12/2022 | Sabadini | C09K 8/58 |
| 2024/0077641 A1* | 3/2024 | Haceb | G01V 11/00 |
| 2024/0254876 A1* | 8/2024 | Katterbauer | E21B 49/00 |

OTHER PUBLICATIONS

Bassinot et al., "Variations of porosity in calcareous sediments from the Ontong Java Plateau," Proceedings of the Ocean Drilling Program, Scientific Results, 1993, 130:653-661, 10 pages.

Beard et al., "Influence of Texture on Porosity and Permeability of Unconsolidated Sand," The American Association of Petroleum Geologists Bulletin, Feb. 1973, 57(2):349-369, 21 pages.

Bond et al., "Construction of tectonic subsidence curves for the early Paleozoic miogeocline, southern Canadian Rocky Mountains: Implications for subsidence mechanisms, age of breakup, and crustal thinning," Geological Society of America Bulletin, Feb. 1984, 95:155-173, 19 pages.

Brown, "Porosity Variation in Carbonates as a Function of Depth: Mississippian Madison Group, Williston Basin," AAPG Memoir 69: Reservoir Quality Prediction in Sandstones and Carbonates, 1997, 29-46, 18 pages.

Budd, "Permeability loss with depth in the Cenozoic carbonate platform of west-central Florida," AAPG Bulletin, Jul. 2001, 85(7):1253-1272, 20 pages.

Croizet et al., "Compaction and porosity reduction in carbonates: A review of observations, theory, and experiments," Advances in Geophysics, Mar. 12, 2013, 54:181-238, 67 pages.

DMT, "DMT CoreScan 3 High-Tech Core Logging Tool," DMT GmbH Exploration & Geosurvey, Jan. 31, 2013, 1-20, 20 pages.

Dunham, "Classification of Carbonate Rocks According to Depositional Texture," AAPG Memoir Classification of Carbonate Rocks—A Symposium, 1962, 108-121, 14 pages.

Ehrenberg, "Assessing the Relative Importance of Compaction Processes and Cementation to Reduction of Porosity in Sandstones: Discussion; Compaction and Porosity Evolution of Pliocene Sandstones, Ventura Basin, California: Discussion," The American Association of Petroleum Geologists Bulletin, Oct. 1989, 73(10):1274-1276, 3 pages.

Embry et al., "A Late Devonian reef tract on northeastern Banks Island, N.W.T.," Bulletin of Canadian Petroleum Geology, Dec. 1971, 19(4):730-781, 52 pages.

Enos et al., "Pore Networks in Holocene Carbonate Sediments," Journal of Sedimentary Petrology, Sep. 1981, 51(3):0961-0985, 25 pages.

Gaillot et al., "Contribution of Borehole Digital Imagery in Core-Log-Seismic Integration," Scientific Drilling, Sep. 2007, 5:50-53, 4 pages.

Goldhammer, "Compaction and Decompaction Algorithms for Sedimentary Carbonates," Journal of Sedimentary Research, Jan. 1997, 67(1):26-35, 10 pages.

Lander et al., "Predicting Porosity through Simulating Sandstone Compaction and Quartz Cementation," AAPG Bulletin, Mar. 1999, 83(3):433-449, 17 pages.

Lee et al., "Quantitative compaction trends of Miocene to Holocene carbonates off the west coast of Australia," Australian Journal of Earth Sciences, Apr. 7, 2021, 68(8):1149-1161, 13 pages.

Ludwick, "A volumeter for measuring porosity of incoherent sands," Journal of Sedimentary Petrology, Sep. 1956, 26(3):276-283, 8 pages.

Malki et al., "Underlying mechanisms and controlling factors of carbonate reservoir characterization from rock physics perspective: A comprehensive review," Geoenergy Science and Engineering, Apr. 6, 2023, 226(211793), 24 pages.

Microfacies of Carbonate Rocks: Analysis, Interpretation and Application, 2nd ed., Flugel et al., 2010, 1028 pages.

Paulsen et al., "A simple method for orienting drill core by correlating features in whole-core scans and oriented borehole-wall imagery," Journal of Structural Geology, Aug. 2002, 24(8):1233-1238, 6 pages.

Scherer, "Parameters Influencing Porosity in Sandstones: A Model for Sandstone Porosity Prediction," The American Association of Petroleum Geologists Bulletin, May 1987, 71(5):485-491, 8 pages.

Schmoker et al., "Carbonate Porosity Versus Depth: A Predictable Relation for South Florida," The American Association of Petroleum Geologists Bulletin, Dec. 1982, 66(12):2561-2570, 10 pages.

Schmoker, "Empirical Relation Between Carbonate Porosity and Thermal Maturity: An Approach to Regional Porosity Prediction," The American Association of Petroleum Geologists, Nov. 1984, 68(11):1697-1703, 7 pages.

Teagle et al., "Methods," Proceedings of the Integrated Ocean Drilling Program, 2006, 309/312, 70 pages.

Tolstaya et al., "Fast Reservoir Characterization with AI-Based Lithology Prediction Using Drill Cuttings Images and Noisy Labels," Journal of Imaging, Jun. 21, 2023, 9(126), 15 pages.

Wang et al., "Influence of the vol. loss of framework grains on the quantitative analysis of diagenetic modification of the original intergranular porosity," Marine and Petroleum Geology, Oct. 27, 2011, 30(1):26-31, 6 pages.

WellCAD Software, "Book 1—Basics," Advanced Logic Technology, Oct. 17, 2011, 4.4:10-11 and 25-27, 11 pages.

Wilkens et al., "Data report: digital core images as data: an example from IODP Expedition 303," Proceedings of the Integrated Ocean Drilling Program, 2009, 303/306, 16 pages.

Wilson et al., "Compaction and Porosity Evolution of Pliocene Sandstones, Ventura Beach, California," The American Association of Petroleum Geologists Bulletin, Jun. 1988, 72(6):664-681, 18 pages.

Worden et al., "Petroleum reservoir quality prediction: overview and contrasting approaches from sandstone and carbonate communities," The Geological Society of London, May 1, 2018, 435, 31 pages.

Zhang et al., "Modeling carbonate diagenesis for reservoir quality prediction: Predicting cementation and compaction from mud content using petrographic data from carbonate reservoir in a giant oil field," AAPG, Aug. 3, 2016, 1 page, (Abstract Only).

* cited by examiner

HYDROCARBON EXPLORATION AND PRODUCTION USING POROSITY VARIATION PREDICTION BASED ON CARBONATE TEXTURE

TECHNICAL FIELD

The present disclosure relates to wellbore drilling, such as for hydrocarbon extraction. More specifically, the disclosure describes techniques for estimating reservoir porosity as a function of depth based on analysis of texture of carbonate rocks.

BACKGROUND

For carbonate formations, understanding the mechanical compaction and porosity-depth relationship is crucial for geosciences and energy resources management such as hydrocarbon exploration and production, as well as carbon capture, utilization, and storage. Carbonate features significant internal heterogeneity in terms of lithofacies and petrophysical properties, thereby presenting unique challenges in porosity prediction, directly impacting the assessment of subsurface energy resources.

SUMMARY

Certain aspects of the subject matter herein can be implemented as a method for hydrocarbon production from a carbonate formation. The method includes, for each reference rock sample of a plurality of reference rock samples of the carbonate formation and based on a determined carbonate grain fraction of the reference rock sample, assigning a respective pre-defined carbonate grain fraction of the reference rock sample that is one of a set of pre-defined carbonate grain fractions. Each reference rock sample is taken from a respective depth of a plurality of depths of the carbonate formation. The method further includes determining a porosity of each reference rock sample of the plurality of reference rock samples taken from the first wellbore, performing a regression analysis using, as inputs, the respective depth, the porosity, and the respective pre-defined carbonate grain fraction assigned to each reference rock sample of the plurality of reference rock samples, to determine the coefficients a, b, c, and d in the following equation:

$$\emptyset(Z,G) = \emptyset_0 \times e^{a \cdot Z} + b \cdot G + c \cdot G \cdot e^{d \cdot Z} + e$$

where $\emptyset(Z, G)$ is the porosity of the sample, $\emptyset_0$ is the initial porosity at the surface; G is the assigned pre-defined carbonate grain fraction assigned to the cutting; and Z is the respective depth from which respective rock sample is taken. The method further includes taking a drill cutting from a wellbore drilled into the carbonate formation, assigning a pre-defined carbonate grain fraction to the drill cutting from the set of pre-defined carbonate grain fractions, and, based on the pre-defined grain fraction assigned to the drill cutting and a depth of the wellbore from which the drill cutting is taken, determining a porosity of the drill cutting using the equation.

Certain aspects of the subject matter herein can be implemented as a method for hydrocarbon production from a carbonate formation including receiving a carbonate texture description determined for a drill cutting taken from a wellbore drilled into the carbonate formation. The carbonate texture description is one of a set of carbonate texture descriptions and is based on an estimate of grain fraction of the drill cutting. The method further includes assigning, based on the received carbonate texture description, a pre-defined grain fraction to the drill cutting. The pre-defined grain fraction is one of a set of pre-defined grain fractions and each pre-defined grain fraction of the set of pre-defined grain fractions corresponds to a respective one the set of carbonate texture descriptions. Based on the pre-defined grain fraction assigned to the drill cutting and a depth of the wellbore from which the drill cutting is taken, an estimated porosity of the drill cutting is determined using the following equation:

$$\emptyset(Z,G) = \emptyset_0 \times e^{a \cdot Z} + b \cdot G + c \cdot G \cdot e^{d \cdot Z} + e$$

where $\emptyset(Z, G)$ is the porosity of the sample, $\emptyset 0$ is the initial porosity at the surface; G is the assigned pre-defined grain fraction assigned to the cutting; and Z is the depth from which the cutting is taken. The coefficients a, b, c, and d are determined by the following steps: A plurality of reference rock samples are taken from a respective depth of a plurality of depths of the carbonate formation. For each reference rock sample of a plurality of reference rock samples of the carbonate formation, assigning, based on a determined grain fraction of the reference rock sample, a respective pre-defined grain fraction to the reference rock sample, the respective pre-defined grain fraction assigned to the reference rock sample comprising one of the set of pre-defined grain fractions. A porosity of each reference rock sample of the plurality of reference rock samples taken from the first wellbore is determined, and a regression analysis is performed for the equation using, as inputs, the respective depth, the porosity, and the respective pre-defined grain fraction assigned to each reference rock sample of the plurality of reference rock samples. The details of one or more embodiments are set forth in the accompanying drawings and the description below. Other features, objects, and advantages will be apparent from the description and drawings, and from the claims.

The details of one or more embodiments are set forth in the accompanying drawings and the description below. Other features, objects, and advantages will be apparent from the description and drawings, and from the claims.

DESCRIPTION OF DRAWINGS

Like reference numbers and designations in the various drawings indicate like elements.

DETAILED DESCRIPTION

The accurate characterization of carbonate formations in petroleum geology and reservoir engineering is important for optimizing subsurface energy resources exploration and extraction. Such formation, noted for their lateral and vertical internal heterogeneity, poses distinct challenges in accurately estimating porosity, impacting assessments of rock quality and energy potential.

The empirical law of mechanical compaction, often characterized by an exponential decrease in porosity with increasing depth, has been extensively described in literature:

$$\emptyset = \emptyset_0 e^{-kz}$$

This model suggests that porosity (Ø) decreases exponentially with depth (z). Here, $\emptyset_0$ is the initial porosity at the surface, and k is the compaction coefficient, a constant that indicates the rate of porosity decrease with depth. The above empirical laws of mechanical compaction have found significant application in understanding porosity-depth trends in various carbonate formations, such as the Cenozoic platform of West-Central Florida, ooze limestones in the shallow waters of the Ontong Java Plateau, and Miocene to Holocene carbonates off the west coast of Australia. However, the internal heterogeneity and complex diagenetic history of carbonate reservoirs often introduce major uncertainties to these current models. They do not account for the specific textural and compositional variations in carbonate rocks.

In accordance with embodiments of the present disclosure, an innovative, texture-specific mechanical compaction model can be applied for porosity prediction in carbonate formations, providing significant improvements in both resource estimation, extraction, and utilization in the energy industry. Our method is more cost-effective and time-saving than current porosity estimation techniques, such as experimental measurement, well-logging tools (either measurement-while-drilling (MWD) or wireline), or empirical correlations involving a range of variables.

Figure 1:
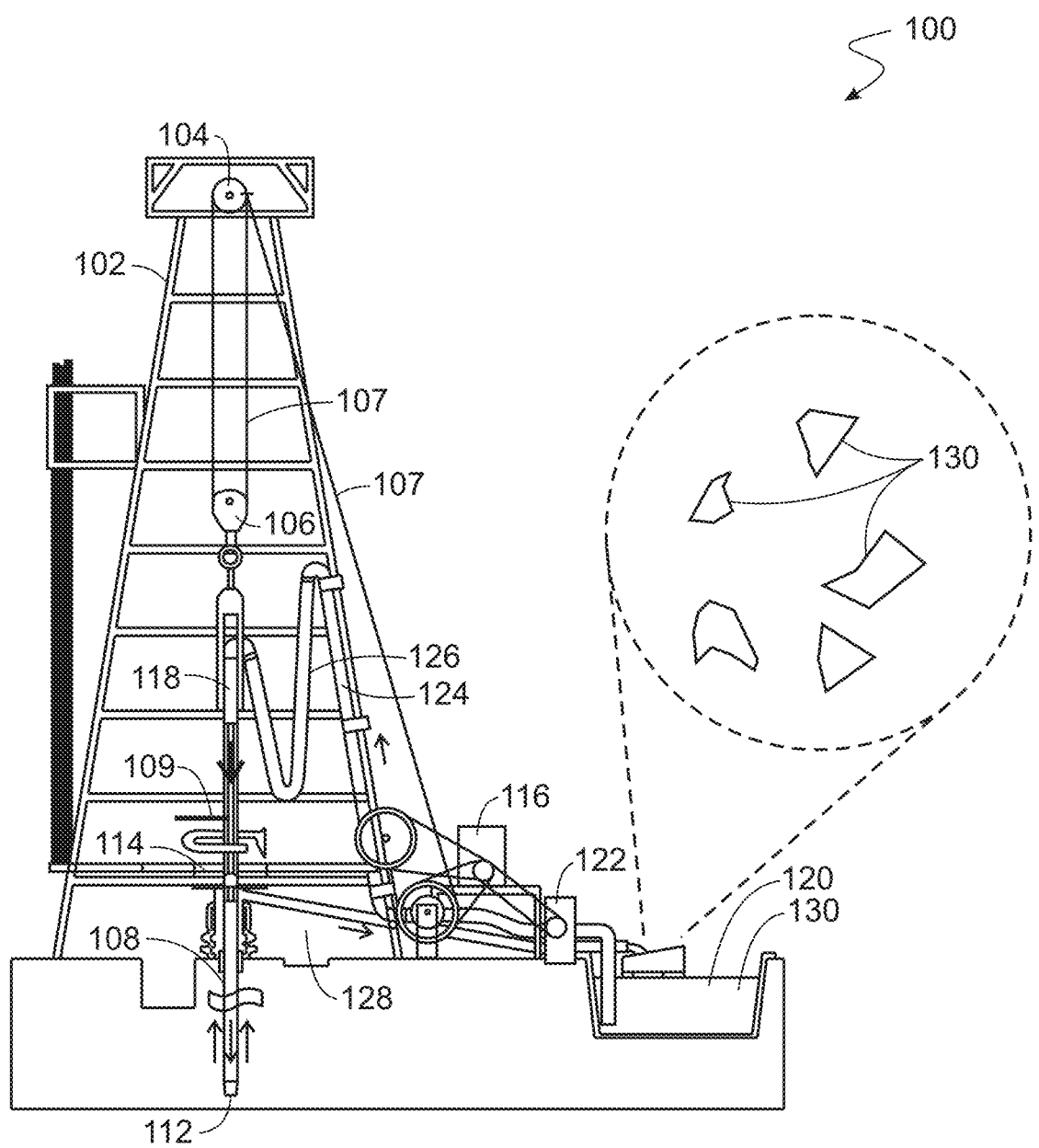
FIG. 1 is an illustration of an example well drilling rig in accordance with one or more embodiments of the present disclosure.

FIG. 1 shows an illustration of an example well drilling rig 100 in accordance with embodiments of the present disclosure. A derrick 102 provides a structure that supports the drilling equipment. A crown block 104 mounted at the top of the derrick 102, a traveling block 106, and a drill line 107 connected between them move the drill string 108 vertically. The drill string 108 includes a plurality of sections of drill pipe 110, a kelly bar 109, and a drill bit 112 or other bottom hole assembly. The kelly bar 109 is a square section of pipe that interfaces with a rotary table 114 to transfer torque from a motor or engine 116 to the drill string 108. A swivel 118 is connected between the top of the drill string 108 and the traveling block 106. The swivel 118 allows the drill string 108 to turn without turning the traveling block 106.

As the drill string 108 rotates, the drill bit 112 engages with and cuts the bottom of the hole penetrating a subsurface formation. The rate at which the drill bit penetrates the formation is called the rate of penetration (ROP). The weight on the drill bit (WOB) is controlled by the amount of tension applied to the drill line 107 and can affect the ROP.

As drilling progresses, mud pump 122 pumps drilling mud 130 from mud tank 120 to the swivel 118 via a rigid standpipe 124 and a flexible hose 126. Drilling mud 130 is pumped through the center of the drill string 108 to the bottom of the hole through the drill bit 112. Drilling mud 130 acts to exert hydrostatic pressure to maintain the integrity of the wellbore and to carry uphole the pieces of formation rock ("cuttings") 132 broken by the drill bit 112 at its downhole end. Drilling mud 130 returns to the surface carrying the cuttings through the annulus formed between the wall of the well and the outside of the drill string 108. Drilling mud 130 returns to the mud tank 120 via a flowline 128 so the mud can recirculate through the system.

As drilling mud 130 circulates, cuttings 132 can be separated from mud 130 at a shale shaker 132 positioned between flowline 128 and mud tank 120. Cuttings 130 can be collected from the shale shaker 132 (or from another suitable location) and can an analyzed for their lithology and other properties. While such analysis can include, for example, chemical or thin-section analysis of lithological or geochemical details, in some instances (for example, in the interests of time constraints) the analysis can include external observation of whole cuttings, either by the naked eye of a wellsite geologist or via an automated visual inspection system. Such an automated visual inspection system can include, for example, a camera and a processing system employing artificial intelligence methods. As described in further detail below, data from such visual inspection can include, for example, description of the texture of the cuttings. The depth from which the cuttings are broken by the drill bit can be calculated or estimated based on, for example, a correlation of the depth of drill bit 112 and the velocity of drilling fluid 130 as it travels through the annulus. In this way, lithological data (for example, rock texture) regarding the formation into which the well is being drilled can be generated in real-time or near real-time.

Determination of targets for petroleum production from carbonate formations generally require determination of suitable porosity and permeability of stratigraphic layers of the formation. Such prediction can be based on, for example, measurements or estimates of porosity of rock samples taken from existing wells. Such porosity data can be extrapolated using known methods of geological and geophysical analysis to locate other subsurface locations within the formation that most likely exhibit the desired combination of porosity and permeability.

In geological analysis of carbonate formations, a simplified definition of carbonate texture can be utilized, based on (for example) the Dunham Classification categories described in Dunham, R. J. (1962) ("Classification of carbonate rocks according to depositional texture (In: Classification of Carbonate Rocks (Ed. W. E. Ham), Am. Assoc. Pet. Geol. Mem., 1) and Fliigel, E., & Munnecke, A. (2010) ("Microfacies of carbonate rocks: analysis, interpretation and application" (Vol. 976). Berlin: springer.) Specifically, the classification can be based on the combined percentage of grain and mud fractions, which together sum up to 100% (excluding volumetrically minor proportions (<10%) of diagenetic products). This binary system allows for a straightforward yet effective representation of carbonate textures, ranging from grain-dominated to mud-dominated compositions. For example, rock sample with a texture with 90% grain and 10% mud can be considered a grainstone, and rock sample with a texture with 10% grain and 90% mud can be considered a mudstone.

Table 1 provides further details of the four Dunham categories.

TABLE 1

| Carbonate type | Lithologic characteristics | Mechanical compaction characteristics |
| --- | --- | --- |
| Grainstone | Well-sorted, grain-supported carbonates with <10% matrix | Lower mechanical compaction with depth compared to carbonates with G values of >10% or mud-support. |
| Packstone | Grain-supported carbonates with >10% matrix | The moderate presence of matrix contributes to porosity reduction but not as extensively as in wackestones or mudstones. |
| Wackestone | Mud-supported carbonates with >10% grains | The compaction significantly reduces porosity and permeability due to higher mud fractions. |
| Mudstone | Mud-supported carbonates with <10% grains | They usually undergo significant porosity loss under limited overburden pressures. |

As described above, generally, porosity decreases with increasing depth. A higher mud fraction results in higher initial porosity at surface, explained partly by the increasing homogeneity and the high water content surrounding grains and filling pores. A higher grain fraction results in a lower rate of decrease in porosity with depth, which means that more rigid grain structures can withstand compaction forces or experience only minor solution at mutual contact surfaces. For simplification, grain fraction and depth can be used as input parameters and porosity as output parameter, and a compaction equation can be derived by multivariate exponential regression analysis, using experimental porosity data from core tests for different Dunham classes to regress the detailed compaction model. Such a model can be expressed as follows:

$$\emptyset(Z,G) = \emptyset_0 \times e^{a \cdot Z} + b \cdot G + c \cdot G \cdot e^{d \cdot Z} + e \quad (1)$$

Wherein $\emptyset_0$ is the initial porosity at the surface, G is the grain fraction, ranging from 0 to 1, Z is the burial depth (in meters), $e^{a \cdot z}$ is an exponential term that accounts for the decrease in porosity with depth (Z), where a is a coefficient that dictates the rate of decrease in porosity with depth (Z), b·G is a linear term where b is a coefficient showing the direct influence of grain fraction (G) on porosity, $c \cdot G \cdot e^{d \cdot Z}$ is a combined term that represents the interaction between grain fraction (G) and depth (Z), with c and d as coefficients modulating this interaction, and e is a constant term that accounts for additional factors or baseline porosity unaffected by grain fraction (G) and depth (Z).

The initial porosity refers to the depositional or primary porosity of the target layer during its early sedimentation stage. The initial porosity may depend on factors such as the depositional environment, particle size and shape of the sediments, and the composition of the sediments. Generally, it can be estimated based on empirical values proposed by various scholars for different depositional environments and sediment types. For instance, the average initial porosity measured by Ludwick ("A Volumeter for Measuring Porosity of Incoherent Sands", Journal of Sedimentary Petrology, VOL. 26, NO. 3, pp. 276-283, September, 1956) on fifty-six beach sand samples was 43%, which could be assigned to the initial porosity for sandstone in beach facies. Alternatively, the initial porosity can be calculated using Scherer's formula (Scherer, "Parameters Influencing Porosity in Sandstones: A Model for Sandstone Porosity Prediction", The American Association of Petroleum Geologists Bulletin, V. 71, No. 5 (May 1987), P. 485-491), derived from Beard and Weyl's wet sand packing experiment data:

$$\emptyset_0 = 20.91 + 22.9/S_0 \quad (2)$$

where $S_0$ is the Trask sorting coefficient, which is the square root of the ratio of the grain size at the 25% cumulative curve to the grain size at the 75% cumulative curve (Beard and Weyl, "Influence of Texture on Porosity and Permeability of Unconsolidated Sand", The American Association of Petroleum Geologists Bulletin, V. 57, No. 2 (February 1973), P. 349-369).

Figure 2:
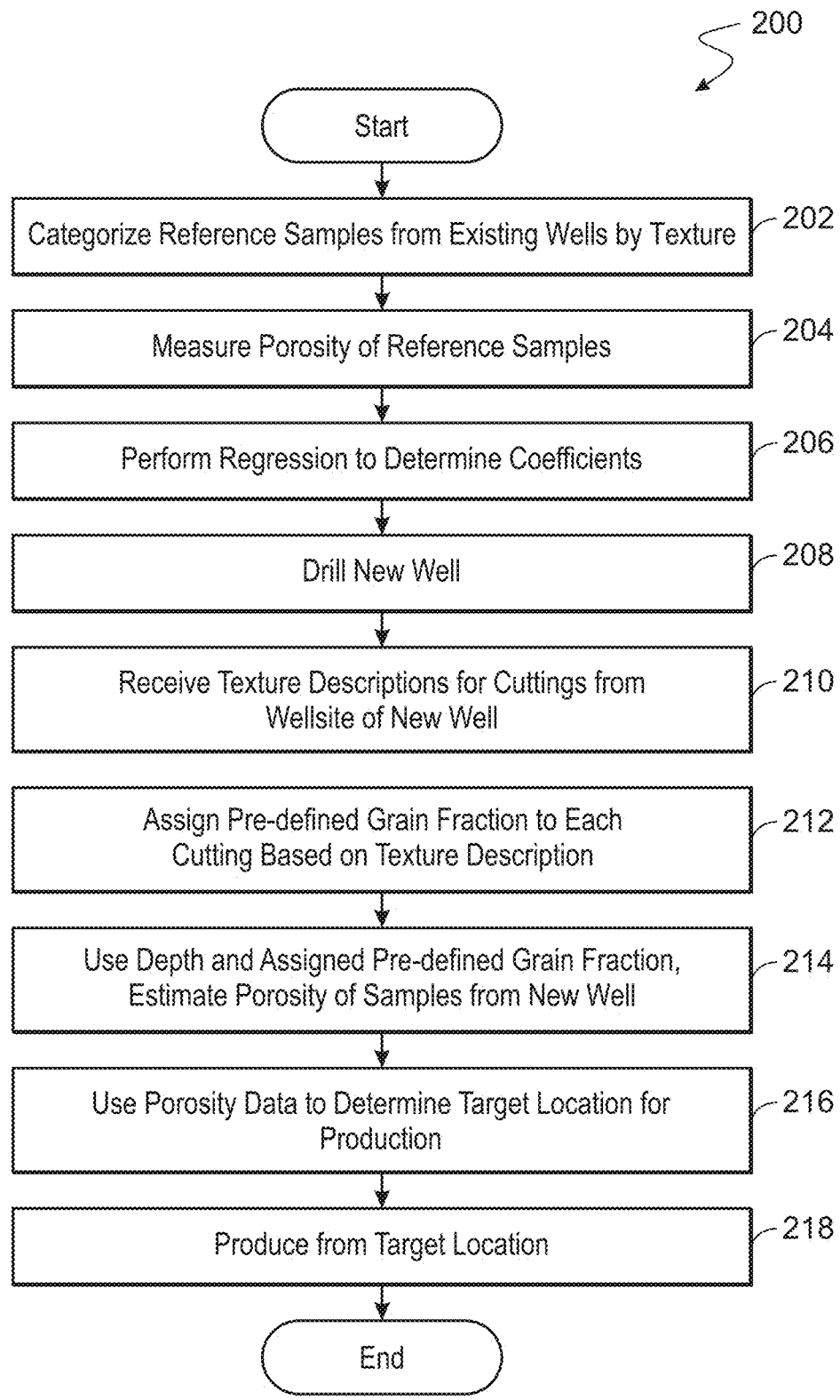
FIG. 2 is an illustration of an example process for hydrocarbon production in accordance with one or more embodiments of the present disclosure.
Figure 3A:
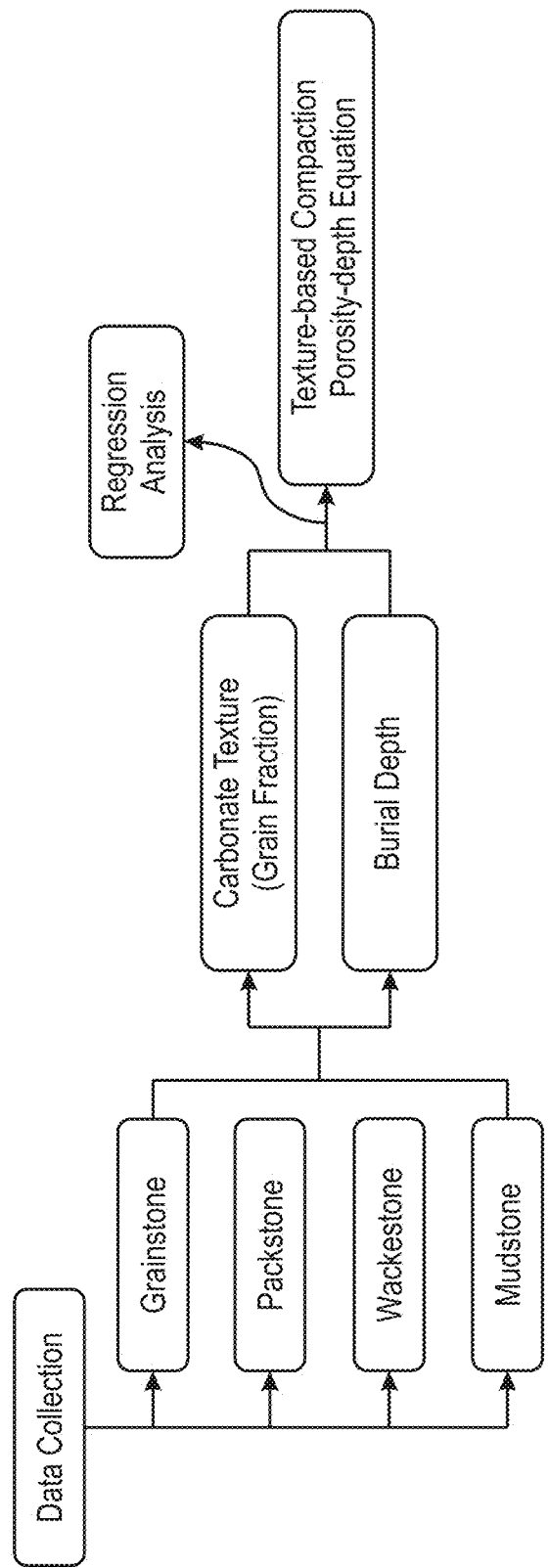
FIGS. 3A and 3B are illustrations of an example workflows for porosity prediction in accordance with one or more embodiments of the present disclosure.

FIG. 2 is an illustration of an example process 200 for porosity prediction in a target carbonate formation in accordance with embodiments of the present disclosure. In some implementations, the process 200 is performed by the data processing systems described herein, such as the data processing system 520 of FIG. 5. Method 200 begins at step 202, in which reference rock samples (for example, core samples) from existing wells in the target reservoir are categorized as having a texture from an appropriate set of textures. An appropriate set of textures can be, for example, the four Dunham textures. The assignment of texture is based in part on the grain fraction determined for each sample. Proceeding to step 204, each of the categorized samples are analyzed for actual porosity (for example, via thin section). From the actual porosity data collected at step 204, coefficients a, b, c, and d are determined at step 206 for equation (1) using regression analysis. In conducting the regression analysis, for each cutting sample with a measured porosity, instead of the actual, determined grain fraction, a grain fraction is inputted that corresponds to one of a finite, limited set of grain fractions pre-defined as corresponding to the respective texture assigned to the sample. For example, in some embodiments, the pre-defined set of grain fractions comprises one of four grain fractions (0.95, 0.90, 0.1, or 0.05), with 0.95 assigned to cuttings categorized as a grainstone, 0.90 assigned to cuttings categorized as a packstone, 0.10 assigned to cuttings categorized as a wackestone, and 0.05 assigned to cuttings categorized as a mudstone. The process of steps 202 through 204 are illustrated schematically in FIG. 3A. In some embodiments, a different texture set other than a Dunham classification system can be utilized, and such a texture set can have a greater or lesser number of textures (for example, three textures or six textures instead of four textures) and the corresponding pre-defined grain fractions can be greater or lesser than those described above for Dunham textures.

At step 208, a new well is drilled into the target carbonate formation. At step 210, as a new well is drilled into the target carbonate formation, external observations of the rock cuttings from this new well are made, as the well drilling proceeds through the stratigraphic layers of the targe reservoir. A carbonate grain fraction is estimated for each sample from the new well based on external observation of the sample. Based on the carbonate grain fraction estimated from external observation, each sample is categorized Such external observations can be made, for example, by naked-eye observation by a geologist at the wellsite, and/or with the use of a camera system combined with an analysis and categorization system that assigns a rock texture classification to an imaged cutting using an artificial intelligence and/or machine learning system. For example, a computer system such as that described in connection with FIG. 5 can be configured to implement a machine learning model such that an estimated grain fraction based on a comparison of an external image of the rock cutting with a training set of rock sample images. The texture may be reported, for example, for each cutting by merely reporting the respecting Dunham category assigned to the cutting.

Proceeding to step 212, each cutting of the new well that has been categorized as having a texture assigned pursuant to step 210 is assigned the corresponding grain fraction from the same finite, limited set of grain fractions applied, at step 206, to the cuttings from the existing wells. For example, if at step 206 a grain fraction of 0.95 has been assigned to cuttings from the existing wells categorized as a grainstone, a grain fraction of 0.90 has been assigned to cuttings from the existing wells categorized as a packstone, a grain fraction of 0.10 has been assigned to cuttings from the new well categorized as a wackestone, and a grain fraction of 0.05 is assigned to cuttings from the existing wells categorized as a mudstone, then, at step 212, a grain fraction of 0.95 is likewise assigned to cuttings from the new well categorized as a grainestone, a grain fraction of 0.90 is likewise assigned to cuttings from the new well categorized as a packstone, a grain fraction of 0.10 is likewise assigned to cuttings from the new well categorized as a wackestone, and a grain fraction of 0.05 is likewise assigned to cuttings from the new well categorized as a mudstone.

Figure 3B:
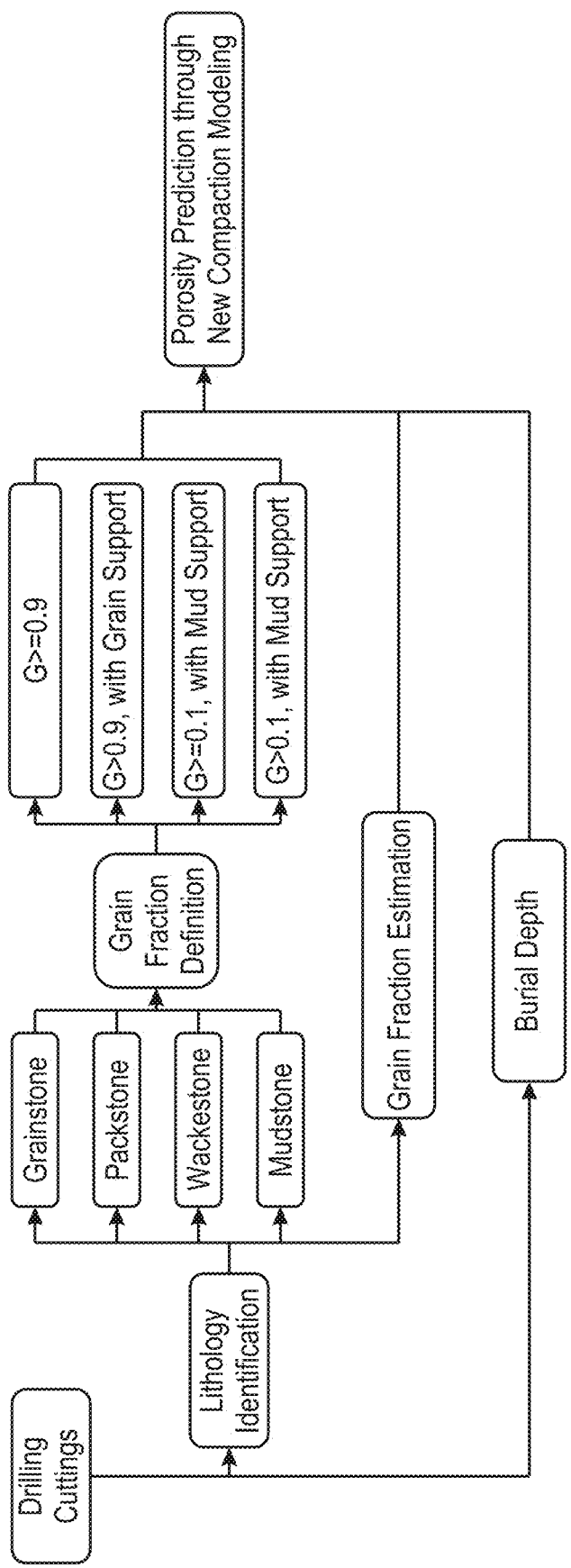
Figure 4A:
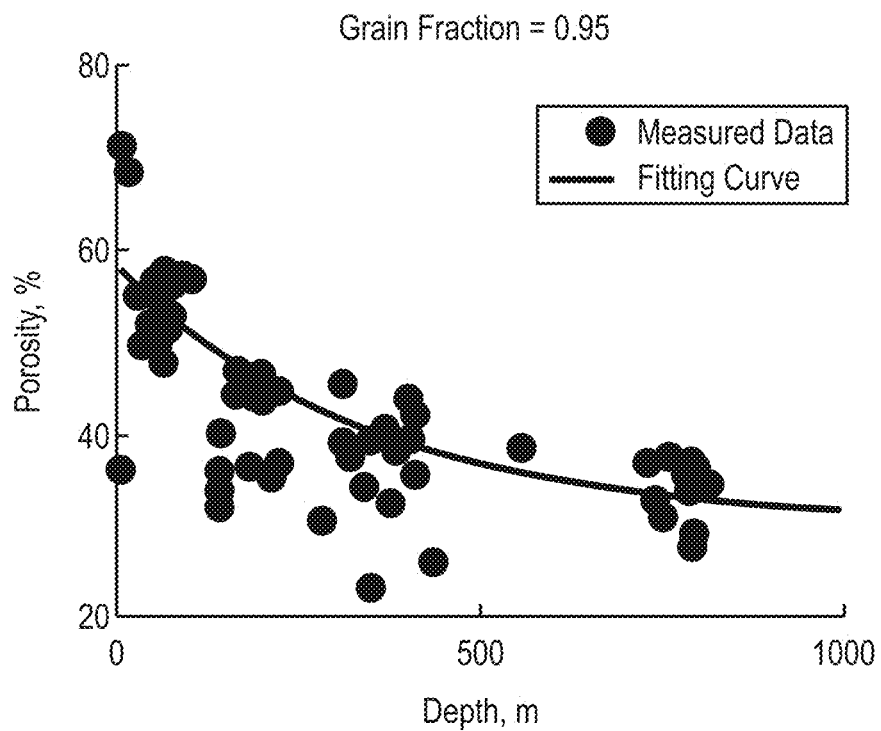
FIGS. 4A-4D are examples of measured porosity variation with depth and predicted porosity curves of carbonates of different textures in accordance with one or more embodiments of the present disclosure.
Figure 4B:
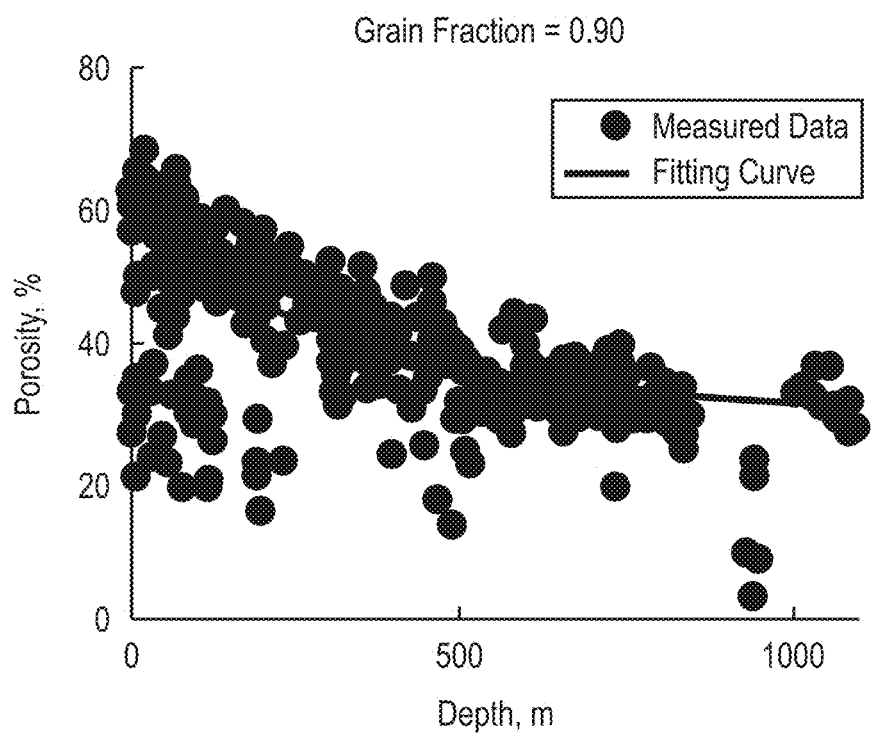
Figure 4C:
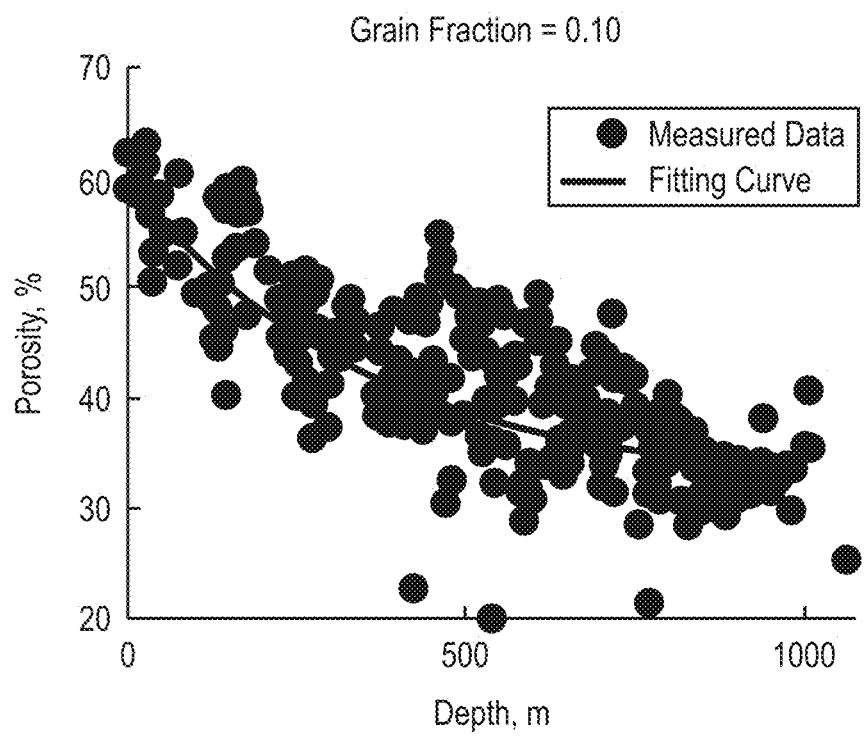
Figure 4D:
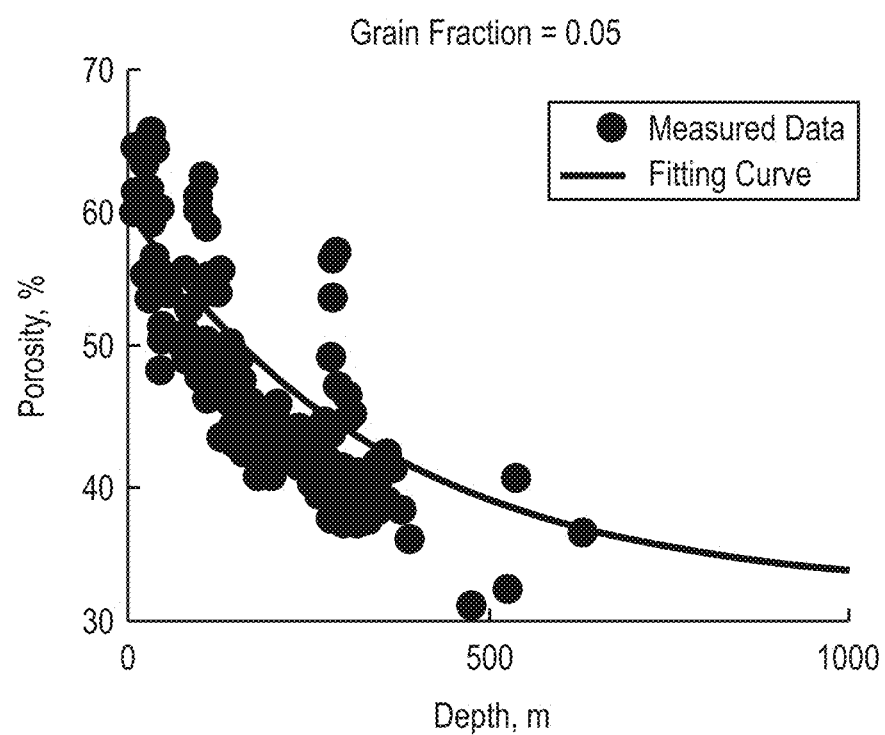

Proceeding to step 214, using equation (1) porosity for each cutting from the new well is predicted (in other words, the porosity of each cutting is estimated) by inputting the assigned grain percent (for example, 0.95, 0.90, 0.10, or 0.05) as G and depth Z for the cutting in question, and solving for porosity, 0, using coefficients a, b, c, and d as determined at step 206. The process of steps 208 through 214 are illustrated schematically in FIG. 3B.

Proceeding to step 216, target subsurface locations in the formation can be determined using geological analysis and based in part on the estimated porosities of the well cuttings and other geological data from the wells drilled into the formation and other geological and geophysical data and analysis. After such target locations have been selected, then, at step 218, wells can be drilled to such target locations and petroleum or other resources can be produced therefrom.

FIGS. 4A-4D are examples of derivations of regression curves measured porosity variation with depth and predicted porosity curves of carbonates of different textures in accordance with one or more embodiments of the present disclosure. The measured porosity values are from samples from a nearly uninterrupted sequence of Miocene to Holocene carbonate sediments extending from the seafloor to approximately 1100 meters core depth below seafloor, on the western shelf of Australia. The samples were collected at Sites U1459-U1464 during the International Ocean Discovery Program (IODP) Expedition 356, known as the Indonesian Throughflow (in Lee, E. Y., Kominz, M., Reuning, L., Gallagher, S. J., Takayanagi, H., Ishiwa, T., Knierzinger W. & Wagreich, M. (2021), Quantitative compaction trends of Miocene to Holocene carbonates off the west coast of Australia, Australian Journal of Earth Sciences, 68:8, 1149-1161). Based on the Dunham Classification, compaction trends across different carbonate textures, including mudstone, wackestone, packstone, and grainstone, have been quantified. The following example assumes specific grain fractions with in the thresholds defined above for each Dunham class grainstone (G=0.95), packstone (G=0.9), wackestone (G=0.1), and mudstone (G=0.05). Combined with the experimental porosity data and measured core depth, the regression formula is calculated as follows:

$$\emptyset(Z,G) = 27.93 \times e^{-0.0029 \times Z} - 2.1672 \times G - 30.8643 \times G \cdot e^{-33.3297 \times z} + 32.17, G \in (0,1)$$

The final compaction equation accords with the geological constrains and fits the experimental data accurately with the $R^2$ value of approximately 0.6, demonstrating that the model can reliably predict porosity in similar carbonate formations. While the defined compaction equation is confirmed within the context of the data used, its applicability to other carbonate settings can be validated with additional data. It is noted that data from samples with strong dolomitic cementation and/or higher proportions of non-skeletal grains that induce strong scatter are excluded from the texture-based compaction trends. The model's performance could vary in varying geological contexts, e.g., sedimentary basin history and associated diagenetic overprint.

Figure 5:
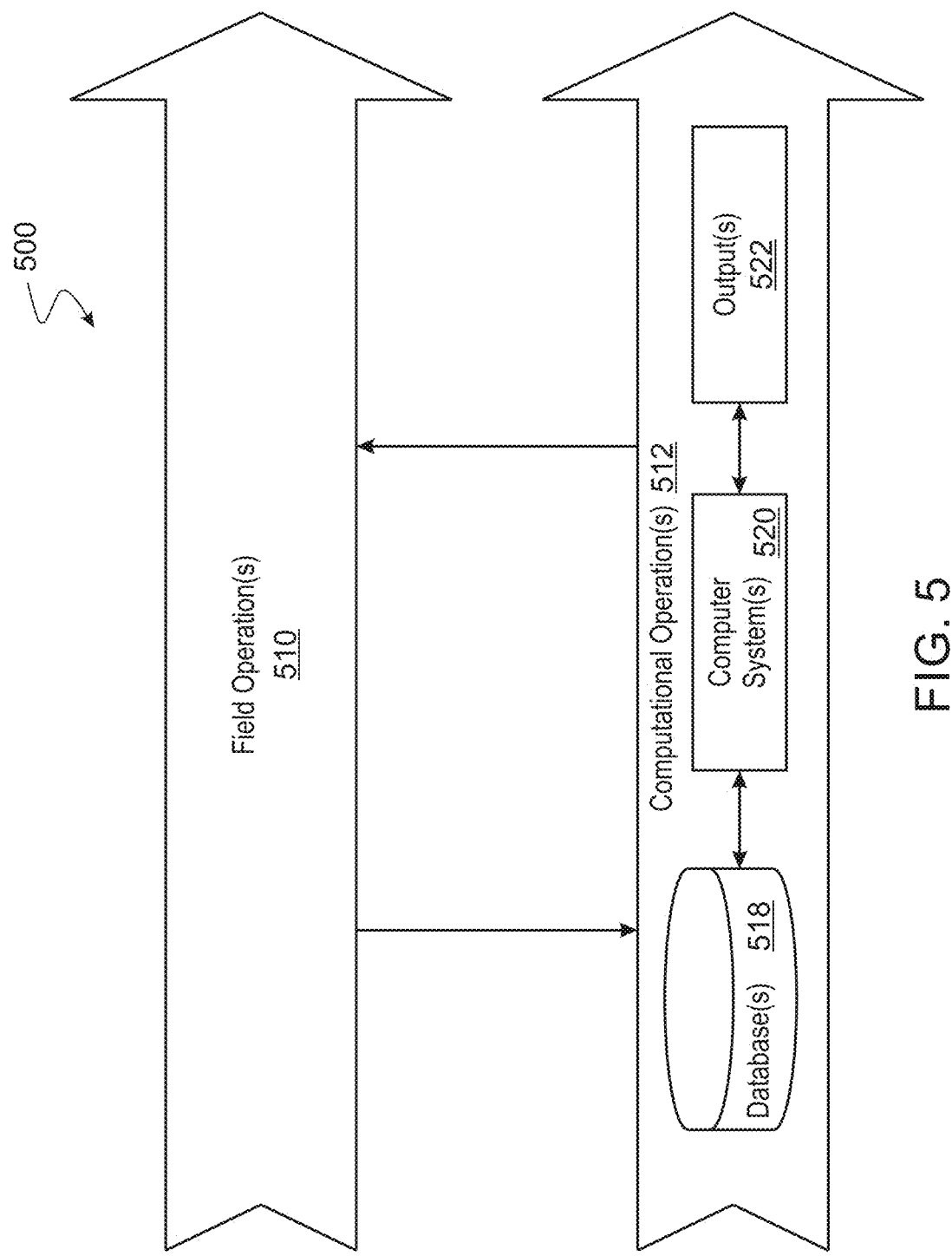
FIG. 5 illustrates hydrocarbon production operations that include both one or more field operations and one or more computational operations, which exchange information and control exploration for the production of hydrocarbons.

FIG. 5 illustrates hydrocarbon production operations 500 that include both one or more field operations 510 and one or more computational operations 512, which exchange information and control exploration for the production of hydrocarbons. In some implementations, outputs of techniques of the present disclosure can be performed before, during, or in combination with the hydrocarbon production operations 500, specifically, for example, either as field operations 510 or computational operations 512, or both.

Examples of field operations 510 include forming/drilling a wellbore, hydraulic fracturing, producing through the wellbore, injecting fluids (such as water) through the wellbore, cuttings retrieval, or cuttings analysis, to name a few. In some implementations, methods of the present disclosure can trigger or control the field operations 510. For example, the methods of the present disclosure can generate data from hardware/software including sensors and physical data gathering equipment (e.g., seismic sensors, well logging tools, flow meters, and temperature and pressure sensors). The methods of the present disclosure can include transmitting the data from the hardware/software to the field operations 510 and responsively triggering the field operations 510 including, for example, generating plans and signals that provide feedback to and control physical components of the field operations 510. Alternatively or in addition, the field operations 510 can trigger the methods of the present disclosure. For example, implementing physical components (including, for example, hardware, such as sensors) deployed in the field operations 510 can generate plans and signals that can be provided as input or feedback (or both) to the methods of the present disclosure.

Examples of computational operations 512 include one or more computer systems 520 that include one or more processors and computer-readable media (e.g., non-transitory computer-readable media) operatively coupled to the one or more processors to execute computer operations to perform the methods of the present disclosure. The computational operations 512 can be implemented using one or more databases 518, which store data received from the field operations 510 and/or generated internally within the computational operations 512 (e.g., by implementing the methods of the present disclosure) or both. For example, the one or more computer systems 520 process inputs from the field operations 510 to assess conditions in the physical world, the outputs of which are stored in the databases 518. For example, seismic sensors of the field operations 510 can be used to perform a seismic survey to map subterranean features, such as facies and faults. In performing a seismic survey, seismic sources (e.g., seismic vibrators or explosions) generate seismic waves that propagate in the earth and seismic receivers (e.g., geophones) measure reflections generated as the seismic waves interact with boundaries between layers of a subsurface formation. The source and received signals are provided to the computational operations 512 where they are stored in the databases 518 and analyzed by the one or more computer systems 520.

In some implementations, one or more outputs 522 generated by the one or more computer systems 520 can be provided as feedback/input to the field operations 510 (either as direct input or stored in the databases 518). The field operations 510 can use the feedback/input to control physical components used to perform the field operations 510 in the real world.

For example, the computational operations 512 can process the seismic data to generate three-dimensional (3D) maps of the subsurface formation. The computational operations 512 can use these 3D maps to provide plans for locating and drilling exploratory wells. In some operations, the exploratory wells are drilled using logging-while-drilling (LWD) techniques which incorporate logging tools into the drill string. LWD techniques can enable the computational operations 512 to process new information about the formation and control the drilling to adjust to the observed conditions in real-time.

The one or more computer systems 520 can update the 3D maps of the subsurface formation as information from one exploration well is received and the computational operations 512 can adjust the location of the next exploration well based on the updated 3D maps. Similarly, the data received from production operations can be used by the computational operations 512 to control components of the production operations. For example, production well and pipeline data can be analyzed to predict slugging in pipelines leading to a refinery and the computational operations 512 can control machine operated valves upstream of the refinery to reduce the likelihood of plant disruptions that run the risk of taking the plant offline.

In some implementations of the computational operations 512, customized user interfaces can present intermediate or final results of the above-described processes to a user. Information can be presented in one or more textual, tabular, or graphical formats, such as through a dashboard. The information can be presented at one or more on-site locations (such as at an oil well or other facility), on the Internet (such as on a webpage), on a mobile application (or app), or at a central processing facility.

The presented information can include feedback, such as changes in parameters or processing inputs, that the user can select to improve a production environment, such as in the exploration, production, and/or testing of petrochemical processes or facilities. For example, the feedback can include parameters that, when selected by the user, can cause a change to, or an improvement in, drilling parameters (including drill bit speed and direction) or overall production of a gas or oil well. The feedback, when implemented by the user, can improve the speed and accuracy of calculations, streamline processes, improve models, and solve problems related to efficiency, performance, safety, reliability, costs, downtime, and the need for human interaction.

In some implementations, the feedback can be implemented in real-time, such as to provide an immediate or near-immediate change in operations or in a model. The term real-time (or similar terms as understood by one of ordinary skill in the art) means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second (s), or less than 5 s. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

Events can include readings or measurements captured by downhole equipment such as sensors, pumps, bottom hole assemblies, or other equipment. The readings or measurements can be analyzed at the surface, such as by using applications that can include modeling applications and machine learning. The analysis can be used to generate changes to settings of downhole equipment, such as drilling equipment. In some implementations, values of parameters or other variables that are determined can be used automatically (such as through using rules) to implement changes in oil or gas well exploration, production/drilling, or testing. For example, outputs of the present disclosure can be used as inputs to other equipment and/or systems at a facility. This can be especially useful for systems or various pieces of equipment that are located several meters or several miles apart, or are located in different countries or other jurisdictions.

Several implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is applicable to at least a computer-implemented method; a non-transitory, computer-readable medium storing computer-readable instructions to perform the computer-implemented method; and a computer system comprising a computer memory inter-operably coupled with a hardware processor configured to perform the computer-implemented method or the instructions stored on the non-transitory, computer-readable medium.

Several embodiments have been described. Nevertheless, it will be understood that various modifications may be made without departing from the scope of the present disclosure. Accordingly, other embodiments are within the scope of the following claims.

EXAMPLES

In a first aspect, a method for hydrocarbon production from a carbonate formation includes, for each reference rock sample of a plurality of reference rock samples of the carbonate formation and based on a determined carbonate grain fraction of the reference rock sample, assigning a respective pre-defined carbonate grain fraction of the reference rock sample that is one of a set of pre-defined carbonate grain fractions. Each reference rock sample is taken from a respective depth of a plurality of depths of the carbonate formation. The method further includes determining a porosity of each reference rock sample of the plurality of reference rock samples taken from the first wellbore, performing a regression analysis using, as inputs, the respective depth, the porosity, and the respective pre-defined carbonate grain fraction assigned to each reference rock sample of the plurality of reference rock samples, to determine the coefficients a, b, c, and d in the following equation:

$$\emptyset(Z,G) = \emptyset_0 \times e^{a \cdot z} + b \cdot G + c \cdot G \cdot e^{d \cdot z} + e$$

where Ø(Z, C) is the porosity of the sample, $\emptyset_0$ is the initial porosity at the surface; G is the assigned pre-defined carbonate grain fraction assigned to the cutting; and Z is the respective depth from which respective rock sample is taken. The method further includes taking a drill cutting from a wellbore drilled into the carbonate formation, assigning a pre-defined carbonate grain fraction to the drill cutting from the set of pre-defined carbonate grain fractions, and, based on the pre-defined grain fraction assigned to the drill cutting and a depth of the wellbore from which the drill cutting is taken, determining a porosity of the drill cutting using the equation.

In a second aspect in accordance with the first aspect, the method further includes determining a target subsurface location for production of hydrocarbons from the carbonate formation based at least in part on the estimated porosity of the cuttings.

In a third aspect in accordance with the first or second aspects, the method further includes producing hydrocarbons from the target subsurface location.

In a fourth aspect in accordance with any of the first through third aspects, the method further includes determining an estimated carbonate grain fraction of the drill cutting based on an external observation of the drill cutting, and assigning a carbonate texture description to the drill cutting based on the estimated carbonate grain fraction. The carbonate texture description assigned to the drill cutting is one of a set of carbonate texture descriptions, and each pre-defined carbonate grain fraction of the set of pre-defined carbonate grain fractions corresponds to a respective one the set of carbonate texture descriptions. The assigning the pre-defined carbonate grain fraction to the drill cutting includes assigning to the drill cutting the pre-defined carbonate grain fraction corresponding to the carbonate texture description assigned to the rock cutting.

In a fifth aspect in accordance with the fourth aspect, the set of carbonate texture descriptions comprises Duhnam textures. In this fifth aspect, a pre-defined carbonate grain fraction corresponding to grainstone is 0.95, a pre-defined carbonate grain fraction corresponding to packstone is 0.90, a pre-defined carbonate grain fraction corresponding to wackestone is 0.10; and a pre-defined carbonate grain fraction corresponding to mudstone is 0.05.

In a sixth aspect in accordance with the fourth aspect, the external observation of the drill cutting is at the wellsite from which the wellbore is drilled.

In a seventh aspect in accordance with the fourth aspect, the external observation is naked-eye observation.

In an eighth aspect in accordance with the fourth aspect, the determining the estimated grain fraction of the drill cutting is by a computer configured to implement a machine learning model, and the determining the estimated grain fraction includes determining, by the computer using the machine learning model, the estimated grain fraction based on a comparison of an external image of the rock cutting with a training set of rock sample images.

In a ninth aspect, a method for hydrocarbon production from a carbonate formation includes receiving a carbonate texture description determined for a drill cutting taken from a wellbore drilled into the carbonate formation. The carbonate texture description is one of a set of carbonate texture descriptions and is based on an estimate of grain fraction of the drill cutting. The method further includes assigning, based on the received carbonate texture description, a pre-defined grain fraction to the drill cutting. The pre-defined grain fraction is one of a set of pre-defined grain fractions and each pre-defined grain fraction of the set of pre-defined grain fractions corresponds to a respective one the set of carbonate texture descriptions. Based on the pre-defined grain fraction assigned to the drill cutting and a depth of the wellbore from which the drill cutting is taken, an estimated porosity of the drill cutting is determined using the following equation:

$$\emptyset(Z,G) = \emptyset_0 \times e^{a \cdot Z} + b \cdot G + c \cdot G \cdot e^{d \cdot Z} + e$$

where Ø(Z, G) is the porosity of the sample, Ø0 is the initial porosity at the surface; G is the assigned pre-defined grain fraction assigned to the cutting; and Z is the depth from which the cutting is taken. The coefficients a, b, c, and d are determined by the following steps: A plurality of reference rock samples are taken from a respective depth of a plurality of depths of the carbonate formation. For each reference rock sample of a plurality of reference rock samples of the carbonate formation, assigning, based on a determined grain fraction of the reference rock sample, a respective pre-defined grain fraction to the reference rock sample, the respective pre-defined grain fraction assigned to the reference rock sample comprising one of the set of pre-defined grain fractions. A porosity of each reference rock sample of the plurality of reference rock samples taken from the first wellbore is determined, and a regression analysis is performed for the equation using, as inputs, the respective depth, the porosity, and the respective pre-defined grain fraction assigned to each reference rock sample of the plurality of reference rock samples. The details of one or more embodiments are set forth in the accompanying drawings and the description below. Other features, objects, and advantages will be apparent from the description and drawings, and from the claims.

In a tenth aspect in accordance with the ninth aspect, the method further includes determining a target subsurface location for production of hydrocarbons from the carbonate formation based at least in part on the estimated porosity of the cuttings.

In an eleventh aspect in accordance with the tenth aspect, the method further includes producing hydrocarbons from the target subsurface location.

In a twelfth aspect in accordance with any of the ninth through eleventh aspects, the set of carbonate texture descriptions are Duhnam textures. In this twelfth aspect, a pre-defined carbonate grain fraction corresponding to grainstone is 0.95, a pre-defined carbonate grain fraction corresponding to packstone is 0.90, a pre-defined carbonate grain fraction corresponding to wackestone is 0.10, and a pre-defined carbonate grain fraction corresponding to mudstone is 0.05.

In a thirteenth aspect in accordance with any of the ninth through twelfth aspects, the carbonate texture description determined for a drill cutting is a carbonate texture description determined based on an external observation of the drill cutting.

In a fourteenth aspect in accordance with any of the ninth through thirteenth aspects, the external observation of the drill cutting is at the wellsite from which the wellbore is drilled.

In a fifteenth aspect in accordance with any of the ninth through fourteenth aspects, the external observation is naked-eye observation.

In a sixteenth aspect in accordance with any of the ninth through fifteenth aspects, the estimated grain fraction is estimated by a computer configured to implement a machine learning model and the determining the estimated grain fraction includes determining, by the computer using the machine learning model, the estimated grain fraction based on a comparison of an external image of the rock cutting with a training set of rock sample images.

What is claimed is:

1. A method for hydrocarbon production from a carbonate formation, the method comprising:
    for each reference rock sample of a plurality of reference rock samples of the carbonate formation and based on a determined carbonate grain fraction of the reference rock sample, assigning a respective pre-defined carbonate grain fraction of the reference rock sample comprising one of a set of pre-defined carbonate grain fractions, wherein each reference rock sample is taken from a respective depth of a plurality of depths of the carbonate formation;
    determining a porosity of each reference rock sample of the plurality of reference rock samples taken from the first wellbore;
    performing a regression analysis using, as inputs, the respective depth, the porosity, and the respective pre-defined carbonate grain fraction assigned to each reference rock sample of the plurality of reference rock samples, to determine the coefficients a, b, c, and d in the following equation:

$$Ø(Z,G) = Ø_0 \times e^{a \cdot z} + b \cdot G + c \cdot G \cdot e^{d \cdot Z} + e$$

where $Ø(Z, G)$ is the porosity of the sample, $Ø_0$ is the initial porosity at the surface; G is the assigned pre-defined carbonate grain fraction assigned to the cutting; and Z is the respective depth from which respective rock sample is taken;
    taking a drill cutting from a wellbore drilled into the carbonate formation;
    assigning a pre-defined carbonate grain fraction to the drill cutting from the set of pre-defined carbonate grain fractions; and
    based on the pre-defined grain fraction assigned to the drill cutting and a depth of the wellbore from which the drill cutting is taken, determining a porosity of the drill cutting using the equation.

2. The method of claim 1, further comprising determining a target subsurface location for production of hydrocarbons from the carbonate formation based at least in part on the estimated porosity of the cuttings.

3. The method of claim 2, further comprising producing hydrocarbons from the target subsurface location.

4. The method of claim 1, further comprising:
    determining an estimated carbonate grain fraction of the drill cutting based on an external observation of the drill cutting; and
    assigning a carbonate texture description to the drill cutting based on the estimated carbonate grain fraction, wherein:
        the carbonate texture description assigned to the drill cutting comprises one of a set of carbonate texture descriptions; and
        each pre-defined carbonate grain fraction of the set of pre-defined carbonate grain fractions corresponds to a respective one the set of carbonate texture descriptions; and
        the assigning the pre-defined carbonate grain fraction to the drill cutting comprises assigning to the drill cutting the pre-defined carbonate grain fraction corresponding to the carbonate texture description assigned to the rock cutting.

5. The method of claim 4, wherein the set of carbonate texture descriptions comprises Duhnam textures and wherein:
    a pre-defined carbonate grain fraction corresponding to grainstone is 0.95;
    a pre-defined carbonate grain fraction corresponding to packstone is 0.90;
    a pre-defined carbonate grain fraction corresponding to wackestone is 0.10; and
    a pre-defined carbonate grain fraction corresponding to mudstone is 0.05.

6. The method of claim 4, wherein the external observation of the drill cutting is at the wellsite from which the wellbore is drilled.

7. The method of claim 4, wherein the external observation is naked-eye observation.

8. The method of claim 4, wherein the determining the estimated grain fraction of the drill cutting is by a computer configured to implement a machine learning model and wherein the determining the estimated grain fraction comprises determining, by the computer using the machine learning model, the estimated grain fraction based on a comparison of an external image of the rock cutting with a training set of rock sample images.

9. A method for hydrocarbon production from a carbonate formation, the method comprising:
    receiving a carbonate texture description determined for a drill cutting taken from a wellbore drilled into the carbonate formation, wherein the carbonate texture description comprises one of a set of carbonate texture descriptions and is based on an estimate of grain fraction of the drill cutting;

based on the received carbonate texture description, assigning a pre-defined grain fraction to the drill cutting, wherein the pre-defined grain fraction comprises one of a set of pre-defined grain fractions and wherein each pre-defined grain fraction of the set of pre-defined grain fractions corresponds to a respective one the set of carbonate texture descriptions; and based on the pre-defined grain fraction assigned to the drill cutting and a depth of the wellbore from which the drill cutting is taken, determining an estimated porosity of the drill cutting using the following equation:

$$\emptyset(Z,G) = \emptyset_0 \times e^{a \cdot z} + b \cdot G + c \cdot G \cdot e^{d \cdot Z} + e$$

where $\emptyset(Z; G)$ is the porosity of the sample, $\emptyset_0$ is the initial porosity at the surface; G is the assigned pre-defined grain fraction assigned to the cutting; and Z is the depth from which the cutting is taken, and wherein the coefficients a, b, c, and d are determined by:

for each reference rock sample of a plurality of reference rock samples of the carbonate formation and based on a determined grain fraction of the reference rock sample, assigning a respective pre-defined grain fraction to the reference rock sample, the respective pre-defined grain fraction to the reference rock sample comprising one of the set of pre-defined grain fractions, wherein each reference rock sample is taken from a respective depth of a plurality of depths of the carbonate formation;

determining a porosity of each reference rock sample of the plurality of reference rock samples taken from the first wellbore; and performing a regression analysis for the equation using, as inputs, the respective depth, the porosity, and the respective pre-defined grain fraction assigned to each reference rock sample of the plurality of reference rock samples.

10. The method of claim 9, further comprising determining a target subsurface location for production of hydrocarbons from the carbonate formation based at least in part on the estimated porosity of the cuttings.

11. The method of claim 10, further comprising producing hydrocarbons from the target subsurface location.

12. The method of claim 9, wherein the set of carbonate texture descriptions comprises Duhnam textures and wherein:

a pre-defined carbonate grain fraction corresponding to grainstone is 0.95;

a pre-defined carbonate grain fraction corresponding to packstone is 0.90;

a pre-defined carbonate grain fraction corresponding to wackestone is 0.10; and a pre-defined carbonate grain fraction corresponding to mudstone is 0.05.

13. The method of claim 9, wherein the carbonate texture description determined for a drill cutting comprises a carbonate texture description determined based on an external observation of the drill cutting.

14. The method of claim 13, wherein the external observation of the drill cutting is at the wellsite from which the wellbore is drilled.

15. The method of claim 13, wherein the external observation is naked-eye observation.

16. The method of claim 9, wherein the estimated grain fraction is estimated by a computer configured to implement a machine learning model and wherein the determining the estimated grain fraction comprises determining, by the computer using the machine learning model, the estimated grain fraction based on a comparison of an external image of the rock cutting with a training set of rock sample images.

* * * * *